US008158588B2

(12) United States Patent
Delagrave

(10) Patent No.: US 8,158,588 B2
(45) Date of Patent: Apr. 17, 2012

(54) LOOP-VARIANT PDZ DOMAINS AS BIOTHERAPEUTICS, DIAGNOSTICS AND RESEARCH REAGENTS

(76) Inventor: Simon Delagrave, Stoneham, MA (US)

( * ) Notice: Subject to any disclaimer, the term of this patent is extended or adjusted under 35 U.S.C. 154(b) by 621 days.

(21) Appl. No.: 12/096,099

(22) PCT Filed: Dec. 4, 2006

(86) PCT No.: PCT/US2006/046310
§ 371 (c)(1),
(2), (4) Date: Jul. 23, 2008

(87) PCT Pub. No.: WO2008/024128
PCT Pub. Date: Feb. 28, 2008

(65) Prior Publication Data
US 2008/0311042 A1    Dec. 18, 2008

Related U.S. Application Data

(60) Provisional application No. 60/742,550, filed on Dec. 5, 2005.

(51) Int. Cl.
*A61K 38/16*   (2006.01)
*C12P 19/34*   (2006.01)
(52) U.S. Cl. .................................... 514/21.3; 435/91.1
(58) Field of Classification Search .................. None
See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 4,619,794 | A | 10/1986 | Hauser |
| 5,914,245 | A | 6/1999 | Bylina et al. |
| 6,677,438 | B1 | 1/2004 | Garnett et al. |
| 7,745,391 | B2 * | 6/2010 | Mintz et al. ............... 514/19.3 |
| 2001/0044135 | A1 | 11/2001 | Stahi et al. |
| 2002/0037999 | A1 | 3/2002 | Mayer |
| 2002/0160424 | A1 | 10/2002 | Adler et al. |
| 2003/0049695 | A1 | 3/2003 | Lu et al. |
| 2003/0059827 | A1 | 3/2003 | Gonzalez et al. |
| 2003/0119716 | A1 | 6/2003 | Ho et al. |
| 2004/0018487 | A1 | 1/2004 | Lu et al. |
| 2004/0067534 | A1 | 4/2004 | Delagrave |
| 2007/0218001 | A1 | 9/2007 | Delagrave |

FOREIGN PATENT DOCUMENTS

| | | |
|---|---|---|
| DE | 3218121 | 11/1983 |
| EP | 36676 | 9/1981 |
| EP | 52322 | 6/1982 |
| EP | 58481 | 8/1982 |
| EP | 88046 | 9/1983 |
| EP | 102324 | 3/1984 |
| EP | 133988 | 3/1985 |
| EP | 142641 | 5/1985 |
| EP | 143949 | 6/1985 |

OTHER PUBLICATIONS

H.J.C. Berendsen. A Glimpse of the Holy Grail? Science (1998) 282, pp. 642-643.*
Rudinger. In: Peptide Hormones, JA Parsons, Ed. (1976) 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Ames, et al., *J Biol Chem* 271, 20231-20234 (1996).
Ausubel, F. M. et al. eds. (1987)), Current Protocols in Molecular Biology.
Barbas et al., Proc. Natl. Acad. Sci. USA, 1992, 9, 10164).
Barbas III, C.F. et al., (2001), Phage Display: A Laboratory Manual.
Binz et al., 2005, Nat Biotechnol, 23(10): 1257-68.
Cabral et al., Nature 382:649-652, 1996.
Chen et al., Biotechnology, 1991, 9, 1073-1077.
Chen et al., Proc. Natl. Acad. Sci. USA, 1993, 90, 5618-5622.
Cho et al., Neuron 9:929-942, 1992.
Cohen et al., 1998, J Cell Biol, 142: 129-38.
Compact Oxford English Dictionary definition of disease.
Creighton, (1993), p. 183.
Daniels et al., 1998, Nat Struct Biol, 5: 317-25.
Delagrave et al., Protein Eng., 1993, 6, 327-331.
Doyle et al., Cell .85:1067-1076, 1996.
Epstein et al., Proc. Natl. Acad. Sci. U.S.A., 1985, 82, 3688.
Fan et al., 2002, Neurosignals, 11: 315-21.
Ferrer et al., 2002, Anal Biochem, 301: 207-16.
Ferrer et al., 2005, Protein Eng Des Sel, 18: 165-173).
Fitch, et al., Circulation 100, 2499-2506 (1999).
Freshney ed, R. I. (1987), Animal Cell Culture.
Fuglsang, Protein Expr Purif. 2003, 31:247-9.
Fuh et al., 2000, J. Biol. Chem. 275:21486-91.
Gerard, et al. Complement in allergy and asthma. Curr Opin Immunol 14, 705-708 (2002).
Goldman and Youvan, Biotechnology (N Y), 1992, 10,1557-61.
Hamilton et al., 2003, Protein Sci, 12: 458-67.
Hanes & Pluckthun, Proc. Natl. Acad. Sci. USA, 1997, 94, 4937.
Harlow and Lane eds. (1988), Antibodies, A Laboratory Manual.
Herlyn, et al., Science, 1986, 232:100.
Horton et al., 1990, Biotechniques, 8: 528-35.).
Hung et al., 2002, J Biol Chem, 277: 5699-702.
Humbles, et al. Nature 406, 998-1001 (2000).
Hwang et al., Proc. Natl. Acad. Sci. U.S.A., 1980, 77, 4030.
Im et al., 2003, J Biol Chem, 278: 8501-7.
Inada et al., J. Bioactive Compat. Polymer 5, 343, 1990.
Itoh et al., J. Cell. Biol. 121:491-502, 1993.
Junqueira et al., 2003, Oncogene, 22: 2772-81.
Joo et al., Chem. Biol., 1999, 6, 699-706.
Joo et al., Nature, 1999, 399, 670-673.
Karthikeyan et al., 2001, J Biol Chem, 276: 19683-6.
Kawamoto, et al., J Clin Invest, 114, 399-407 (2004).
Keefe et al., 2001, Nature, 410: 715-8.

(Continued)

*Primary Examiner* — Marcela M Cordero Garcia
(74) *Attorney, Agent, or Firm* — Fish & Richardson P.C.

(57) ABSTRACT

The present invention provides polypeptides that contain one or more PDZ loop-variants and are useful in the detection of pathogens and disease-associated molecules. The polypeptides of the invention are also useful in the diagnosis, treatment, and prevention of diseases. Also provided are methods of preparing polypeptides of the invention.

2 Claims, 3 Drawing Sheets

OTHER PUBLICATIONS

Kim et al., Nature 378:85-88, 1995.
Kornau et al., Science 269:1737-1740, 1995.
Kozlov, G. et al., J. Mol. Biol.. 2002, 320, pp. 813-820.
Langer et al., J. Biomed. Mater. Res., 1981, 15, 167.
Langer, Chem. Tech., 1982, 12, 98.
Legendre et al., 2002, Protein Sci, 11: 1506-18.
Leung et al., Technique, 1989, 1, 11-15.
MacPherson, M. et al. IRL Press at Oxford University Press (1991)), PCR: A Practical Approach.
M. J. MacPherson et al., eds. (1995), PCR 2: A Practical Approach.
Marrs et al., Curr. Opin. Microbiol., 1999, 2, 241-245.
Miyazaki et al., J. Mol. Evol., 1999, 49, 716-720.
Moyer et al., 2000, J Biol Chem, 275(35): 27069-74.
Nicaise et al., 2004, Protein Sci, 13: 1882-91. Epub 2004.
Nucci et al., Advan. Drug Del. Rev. 6, 133, 1991.
Oi, et al., BioTechniques, 1986, 4(3), 214.
Ponting and Phillips, Trends Biochem. Sci. 20:102-103, 1995.
Reina et al., 2002, Nat Struct Biol, 9: 621-7.
Remington's Pharmaceutical Sciences, Chapter 43, 14th Ed., Mack Publishing Co, Easton PA. 18042, USA.
Ronnmark et al., 2002, Eur J Biochem, 269: 2647-55.
Sambrook, et al., Molecular Cloning: A Laboratory Manual, 2nd edition (1989).
Sato et al., Science, vol. 268, 1995.
Shernan, et al., Ann Thorac Surg 77, 942-949 (2004).
Schneider et al., 1999, Nature Biotechnology 17:170-175.
Singh, Nat. Struct.Biol., 2000,7 : 617-9.
Skelton, et al., J. Biol. Chem., 278,(9), pp. 7645-7654, 2003.
Sidman et al., Biopolymers, 1983, 22, 547.
Smith, Science, 1985, 228, 1315.
Spira, et al., J. Immunol. Methods, 1984, 74, 307.
Stemmer et al., Gene, 1993,123:1-7.
Steplewski, et al. Proc. Natl. Acad. Sci., 1985, 82, 8653.
Stubbs, TrendsPharmcol Sci, 2002,23: 539-41.
Wadia and Dowdy, 2002, Curr Op Biotechnol, 13:52-6.
Woods and Bryant, Cell 66:451-464, 1991.
Xu et al., 2002, Chem Biol, 9: 933.
You et al., Protein Eng, 1996, 9, 77-83.
Zeytun et al., 2003, Nat Biotechnol, 21: 1473-9.
International Search report and Written Opinion for PCT/US2006/046310, dated Jun. 7, 2008.

* cited by examiner

FIGURE 1

```
                          10        20        30        40        50        60
                 ....*....|....*....|....*....|....*....|....*....|....*....|
Feature 1                β12 loop          #### #  β23 loop
consensus    1   VRTVTLRKdp--------------dGGLGFSLRGgkds---gggIFVSRVEpGGPAer-  41
3PDZ_A       6   IFEVELAKn--------------dNSLGISVTGgvntsvrhggIYVKAVIpQGAAesd  49
1I92_A       4   PRLCCLEKg--------------pNGYGFHLHGekg----klgQYIRLVEpGSPAek-  42
1KWA_A       2   SRLVQFQKnt--------------dEPMGITLKMnel-----nhCIVARIMhGGMIhrq  41
1PDR         8   PRKVVLHKg--------------sTGLGFNIVGged----gegIFISFILaGGPAdls  47

70        80        90       100       110
                 ....*....|....*....|....*....|....*....|....*....|....*....|
Feature 1                      β5α2 loop  ##   ##    α2β6 loop
consensus   42   -----ggLRVGDRILEVNGVSVegltHEEAVELLKNSgd---------eVTLTVR    82
3PDZ_A      50   -----grIHKGDRVLAVNGVSIegatHKQAVETLRNTgq---------VHLLLE    90
1I92_A      43   -----agLLAGDRLVEVNGENVeketHQQVVSRIRAAln---------eVRLLVV   83
1KWA_A      42   -----gtLHVGDEIREINGISVanqtVEQLQKMLREMrg---------sITFKIV   82
1PDR        48   -----geLRKGDRIISVNSVDLraasHEQAAAALKNAgq---------eVTIVAQ   88
```

LOOP-VARIANT PDZ DOMAINS AS BIOTHERAPEUTICS, DIAGNOSTICS AND RESEARCH REAGENTS

CROSS REFERENCE TO RELATED APPLICATIONS

This application is a 35 USC 371 National Stage application of International Application No. PCT/US2006/046310, filed Dec. 4, 2006, which claims the benefit of U.S. Ser. No. 60/742,550, filed. Dec. 5, 2005.

FIELD OF THE INVENTION

The present invention relates to polypeptides that are useful in methods of detecting pathogens as well as diagnosing and treating diseases. The polypeptides contain at least one PDZ domain loop-variant capable of binding with a target associated with a pathogen or disease state. In vitro evolution processes can be used to prepare the polypeptides of the invention.

BACKGROUND OF THE INVENTION

Availability of proteins that specifically bind or interact with target proteins or other molecules has for some time been of importance in biology and medicine. For example, medical diagnosis has been revolutionized by assays using high-affinity proteins, mainly, antibodies, that bind to disease markers. High-affinity antibodies to disease-causing agents are of increasing importance in medical therapeutics. In biological research, high affinity proteins, also mainly antibodies, have found use in the purification of rare proteins, in the localization of proteins or other antigens in cells such as by immunohistochemical techniques, and in countless other applications. High-affinity proteins are likely to assume increasing importance in the future (Binz et al., 2005, Nat Biotechnol, 23: 1257-68.). For example, the emerging field of proteomics seeks to understand the patterns of expression and interaction of a substantial fraction of the proteins encoded in a cell's genome.

However, existing methods of providing binding proteins or polypeptides that bind with affinity and specificity to selected targets, especially to large numbers of selected targets, has been and continues to be difficult and expensive. The predominant method used today is to raise antibodies, either monoclonal or polyclonal, against a target molecule. Although well known and widely used, this strategy has several limitations and disadvantages (Binz et al., 2005, Nat Biotechnol, 23: 1257-68.). First, to generate, or "raise", an antibody against a target requires either a sufficient amount of the purified target itself or a chemically synthesized fragment of the target. Second, raising an antibody normally requires the use of living animals, and due to species incompatibilities, it is not always possible to raise a specific antibody against a particular target, much less against large numbers of targets, such as a significant fraction of the proteins in an organism. Third, isolation and production of antibodies are expensive, time-consuming and unpredictable processes. Fourth, antibodies cannot be expressed via recombinant hosts without significant investment of time and money because the antigen-binding regions of the antibody heavy and light chains must be cloned, sequenced, and then simultaneously expressed. Finally, antibodies usually do not fold properly in the reductive cell environment, and therefore are not useful to target intracellular molecules involved in disease. Such limitations and disadvantages constitute a significant barrier to the rapid identification, diagnosis and treatment of infectious diseases such as AIDS, SARS, West Nile virus, and anthrax, or of non-infectious diseases such as cancer.

An alternative method relies on "directed evolution" to alter the binding specificity of naturally-occurring proteins that are known to bind to determined targets. In this method, a known gene is randomly mutated by a chemical or biotechnological mutagenesis technique, for example, by PCR-based mutagenesis, or by insertion of randomized codons in regions corresponding to elements of protein secondary structure called "loops", e.g., (Legendre et al., 2002, Protein Sci, 11: 1506-18.), or by randomization of codons that normally constitute a loop (e.g., Xu et al., 2002, Chem Biol, 9: 933), and other references reviewed in (Binz et al., 2005, Nat Biotechnol, 23: 1257-68.). Then a library of the resulting protein variants is screened for variants having affinity to a new target, for example, by phage display. In this way, several proteins have been "evolved" in the laboratory to create protein variants having useful new specificities, e.g., (Xu et al., 2002, Chem Biol, 9: 933), and reviewed in (Binz et al., 2005, Nat Biotechnol, 23: 1257-68.). Alternatively, "loop grafting" wherein an insertion of a preexisting amino acid chain that is known to bind a target molecule of interest is made in one loop of a "scaffold protein", as was done by Nicaise and colleagues (Nicaise et al., 2004, Protein Sci, 13: 1882-91. Epub 2004 May 28.), can also be carried out to confer a novel binding specificity to the scaffold protein.

A further alternative is to create novel binding proteins de novo through directed evolution. However, proteins having no natural counterparts, e.g., iMabs from Catchmabs BV or as described by (Keefe et al., 2001, Nature, 410: 715-8), have significant drawbacks such as, for example, that they are likely to be recognized as foreign by the human immune system, thereby impeding their use as therapeutics. For the same reason, natural proteins of non-human origin engineered to bind target polypeptides (e.g., Ronnmark et al., 2002, Eur J Biochem, 269: 2647-55.; Zeytun et al., 2003, Nat Biotechnol, 21: 1473-9.) are unlikely to be useful as therapeutics or diagnostics.

Thus, the choice of binding protein to be modified via directed evolution will strongly influence the utility of the evolved binding proteins. PDZ domains constitute an example of a family of binding proteins which can be used to create novel research reagents (Ferrer et al., 2005, Protein Eng Des Sel, 18: 165-173), diagnostic reagents or therapeutics having many advantages over existing binding proteins (WO 2005/072159). Such advantages include ease and speed of isolation using in vitro methods, low cost of production using non-mammalian host cells, potential utility as intracellular biotherapeutics due to their natural propensity to function in the cytoplasm, and lack of immunogenicity.

PDZ domains are relatively well understood and of great potential utility. They participate in signal transduction pathways by mediating protein complex formation and are also involved in targeting of proteins to various locations within the cell. In metazoan genomes, including the human genome, PDZ domains are among the most common protein sequence modules. Recent reviews on PDZ domains include refs. (Hung et al., 2002, J Biol Chem, 277: 5699-702) and (Fan et al., 2002, Neurosignals, 11: 315-21). Many PDZ domains are stable and expressed to high levels in recombinant bacterial hosts, which has facilitated their extensive biophysical characterization (e.g., Morais Cabral et al., 1996, Nature, 382: 649-52.; Cohen et al., 1998, J Cell Biol, 142: 129-38.; Daniels et al., 1998, Nat Struct Biol, 5: 317-25.; Im et al., 2003, J Biol Chem, 278: 8501-7). PDZ domains have been described as potential therapeutics, for example to treat cancer by interfering with Myc protein function. See for example, (Junqueira et al., 2003, Oncogene, 22: 2772-81) and US Pat. App. Pub. No. 20030119716. Other PDZ patent applications expand the utility of PDZ domains by describing engineered PDZ domain fusions, or chimeras, with other proteins (US Patent Application Pub. Nos. 20010044135, 20020037999, and 20020160424). PDZ domains can also be used to identify drug candidates in high-throughput screens (Ferrer et al., 2002, Anal Biochem, 301: 207-16; Hamilton et al., 2003, Protein Sci, 12: 458-67) (Ferrer et al., 2005, Protein Eng Des Sel, 18: 165-173).

Some progress has been made in studying and modifying the binding specificity of PDZ domains. Schneider et al., 1999, Nature Biotechnology 17:170-175 and (Junqueira et al., 2003, Oncogene, 22: 2772-81) both describe how the binding specificity of a naturally-occurring PDZ domain can be altered using directed evolution methods. Phage display may be used to determine the specificity of a given PDZ domain (see, e.g., Fuh et al., 2000, J. Biol. Chem. 275:21486-91). In this work, Fuh and colleagues selected phage-displayed random C-terminal peptide sequences capable of binding to an immobilized PDZ domain. However, this approach is not intended to, and cannot alter the specificity of a given PDZ domain. Skelton et al. (2003, J. Biol. Chem., 278: 7645-54), propose the use of phage display to alter PDZ domain specificity, but the paper by Ferrer et al. (Ferrer et al., 2005, Protein Eng Des Sel, 18: 165-173) is the first experimental demonstration of this concept. Phage display is believed to provide greater control over the conditions of the binding interactions, including affinity and specificity, than is afforded by two-hybrid selections which are notoriously artifact-prone.

Alternatively, PDZ domains with altered binding specificity may be designed by computational methods, as shown by (Reina et al., 2002, Nat Struct Biol, 9: 621-7) and US Patent Application Pub. No. 20030059827. These computational methods seem to offer several apparent benefits, such as reduced cost and time by avoiding experimental effort, and scalability for determining binding proteins to multiple targets. On the other hand, these methods have certain notable drawbacks such as the well-known extreme difficulty of predicting binding affinities of designed protein structures, yielding candidate binding proteins of unreliable affinity and specificity. Also, once structures have been designed in silico, the corresponding proteins must still be prepared in the laboratory. The effort required to construct the candidate gene variants is similar to the effort required to prepare a library of mutant genes, and once such a library is constructed, it can be screened multiple times with diverse targets whereas new variants must be designed and synthesized for each new target. Finally, design of variant binding proteins and optimization of their binding affinity is extremely difficult without the availability of detailed information on their atomic structure, while directed evolution has no such need. The acquisition of this type structural data is costly and slow, often requiring months of work.

To fully realize the potential of PDZ domains as diagnostics and therapeutics, the ability to engineer alternative or additional binding sites in PDZ domains is highly desirable. The majority of PDZ domains that have been studied so far bind to the last few (three to seven) residues at the carboxyl terminus of their cognate polypeptide ligands. However, because a significant fraction of molecular targets have inaccessible carboxyl termini or termini that do not participate in disease mechanisms, PDZ variants capable of binding other features of target proteins would have desirable versatility and utility as research reagents, diagnostic reagents, and therapeutics.

In summary, polypeptides capable of binding to specific targets, especially to natural peptide sequences, are useful in biology and medicine, and are expected to be of increasing utility in the future. Therefore, inexpensive and efficient methods for providing diverse binding proteins capable of functioning as affinity reagents and/or therapeutics are needed.

SUMMARY OF THE INVENTION

The present invention provides a polypeptide comprising PDZ loop-variant, wherein the PDZ loop-variant comprises one or more amino acid insertions or substitutions in at least one of loops $\beta12$, $\alpha2\beta6$, $\alpha23$, and $\beta5\alpha2$. In some embodiments, the PDZ loop-variant comprises one or more amino acid insertions or substitutions in at least one of loops $\beta23$ and $\beta5\alpha2$. In some embodiments, the PDZ loop-variant comprises one or more amino acid insertions or substitutions in loop $\beta23$. In some embodiments, the PDZ loop-variant comprises one or more amino acid insertions in loop $\beta23$. In some embodiments, the PDZ loop-variant comprises one or more amino acid substitutions in loop $\beta23$. In some embodiments, the PDZ loop-variant binds to a target. In some embodiments, the target is associated with a pathogen or disease state.

The present invention further provides a polynucleotide encoding a polypeptide of the invention, or a host cell comprising the polynucleotide.

The present invention further provides a method of preparing a polypeptide of the invention, comprising the steps of:
a) creating a library of polypeptide PDZ loop-variants; and
b) identifying one or more polypeptides of the library having binding affinity for a molecular target. In some embodiments, the target is associated with a pathogen or disease.

The present invention further provides a method of detecting the presence of a pathogen or disease in a patient comprising the steps of:
a) administering a polypeptide of the invention to the patient; and
b) detecting binding or absence of binding of the polypeptide to a target which is associated with the pathogen or disease in the patient, wherein detection of binding indicates the presence of the pathogen or disease, and wherein absence of binding indicates the absence of the pathogen or disease.

The present invention further provides a method of detecting the presence of a pathogen or disease in a sample comprising the steps of:
a) contacting a polypeptide of the invention with the sample; and
b) detecting binding or absence of binding of the polypeptide to a target which is associated with the pathogen or disease in the sample, wherein detection of binding indicates the presence of the pathogen or disease and wherein absence of binding indicates the absence of the pathogen or disease.

The present invention further provides a method of treating a disease, comprising administering to a patient afflicted with or likely to be afflicted with the disease a therapeutically effective amount of a polypeptide of the invention capable of binding to a target associated with the disease. In some embodiments, the disease is associated with a pathogen.

The present invention further provides a library of polypeptide PDZ loop-variants.

The present invention further provides a library of polynucleotides encoding the library of polypeptide PDZ loop-variants.

The present invention further provides an isolated polypeptide of the invention that is bivalent.

The present invention further provides a method of detecting the presence of a pathogen or disease in a patient comprising the steps of:

a) administering a bivalent polypeptide of the invention to the patient; and b) detecting binding or absence of binding of the bivalent polypeptide to a target which is associated with the pathogen or disease in the patient, wherein detection of binding indicates the presence of the pathogen or disease, and wherein absence of binding indicates the absence of the pathogen or disease.

The present invention further provides a method of detecting the presence of a pathogen or disease in a sample comprising the steps of:

a) contacting a bivalent polypeptide of the invention with the sample; and b) detecting binding or absence of binding of the bivalent polypeptide to a target which is associated with the pathogen or disease in the sample, wherein detection of binding indicates the presence of the pathogen or disease and wherein absence of binding indicates the absence of the pathogen or disease.

The present invention further provides a method of treating a disease, comprising administering to a patient afflicted with or likely to be afflicted with the disease a therapeutically effective amount of a bivalent polypeptide of the invention capable of binding to a target associated with the disease. In some embodiments, the disease is associated with a pathogen.

The present invention further provides a polynucleotide comprising the nucleotide sequence of SEQ ID NO 22.

The present invention further provides a library of polynucleotides wherein members of the library comprise the nucleotide sequence of SEQ ID NO 22.

BRIEF DESCRIPTION OF THE DRAWINGS

FIG. 1. Conserved Domains Database (CDD, maintained by NCBI, www.ncbi.nlm.nih.gov/entrez/query.fcgi?db=cdd) output showing alignment of PDZ domains, including Hptp1E (3PDZ A) (SED ID NO: 1), hCASK (1KWA_A) (SEQ ID NO: 2), NHERF (1I92_A) (SEQ ID NO: 3), and PDZ3 of human Dlg1 (1PDR) (SEQ ID NO:4). Loops β12, α2β6, β23, and β5α2, are shown (boxed) in the alignment and in FIG. 2. Consensus PDZ sequence alignment is SEQ ID NO: 23.

DETAILED DESCRIPTION

Figure 2:
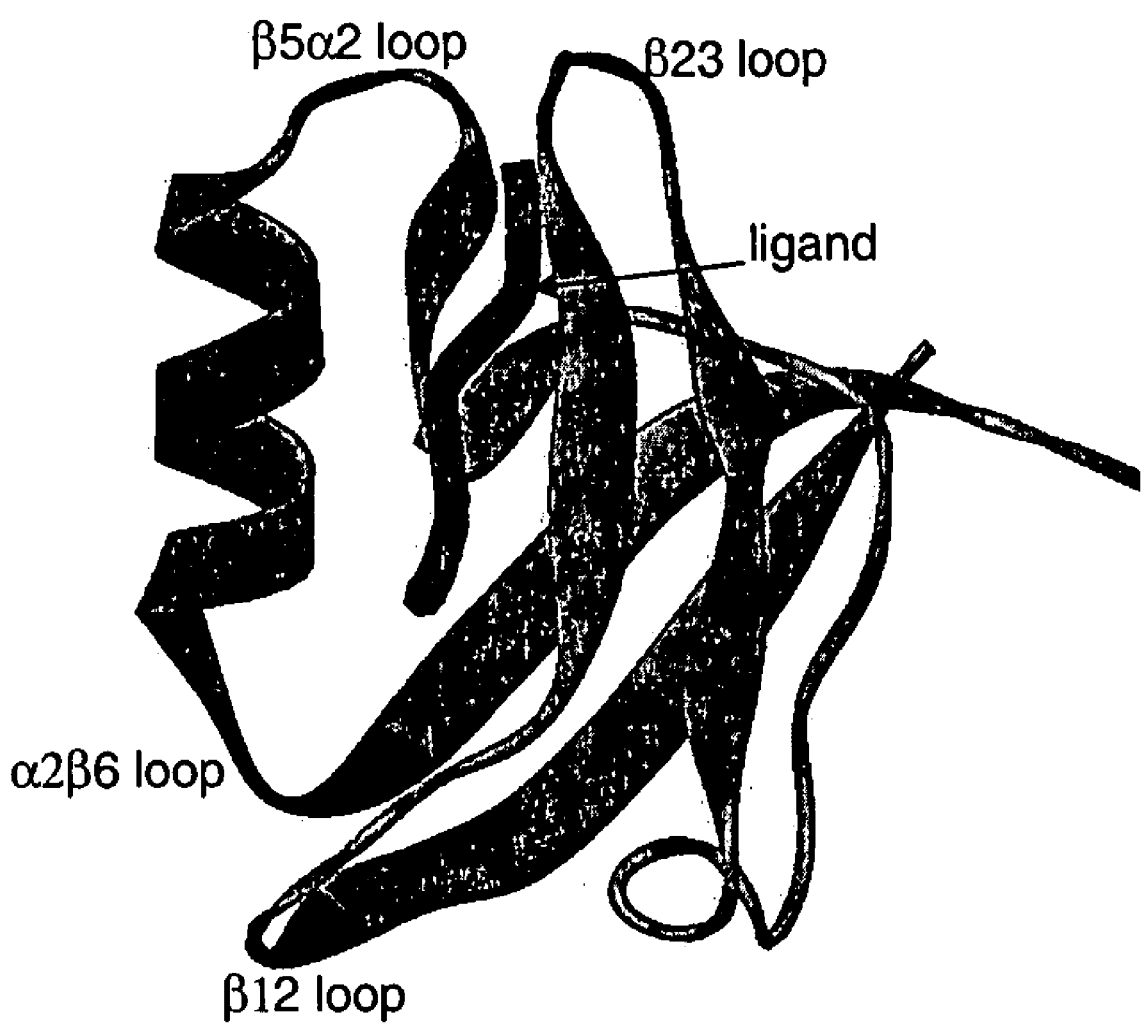
FIG. 2. Loops β12, α2β6, β23, and β5α2, are shown in this structure of hCASK PDZ (protein databank number 1KWA). The same residues are boxed in the alignment of FIG. 1.

The present invention provides, inter alia, a polypeptide comprising one or more loop-variant PDZ domains capable of binding to a preselected target, and methods of using and preparing the polypeptide. In some embodiments, the loop-variant PDZ domain is engineered. In some embodiments, at least one of the one or more loop-variant PDZ domains binds to a target produced by a pathogen or disease state. In further embodiments, the polypeptide comprises two PDZ domains, advantageously resulting in a PDZ dimer that binds to a target polypeptide with greater avidity than a polypeptide containing only one PDZ domain. Example targets include naturally and non-naturally occurring proteins, peptides, or other molecules associated with, such as are associated with (e.g., produced directly or indirectly by), a pathogen or disease state, including non-infectious disease states such as cancer, neurodegeneration, and cardiopulmonary dysfunction.

Definitions

As used herein, "polypeptides" or "proteins" are polymers of amino acids having, for example, from 2 to about 1000 or more amino acid residues. In some embodiments, "polypeptides" have from 10 to about 250 amino acids, or from about 15 about 200 amino acids. Any naturally occurring or synthetic amino acid can form the polypeptide. Polypeptides can also include modifications such as glycosylations and other moieties. In some embodiments, polypeptides of the invention have the ability to selectively bind to target polypeptides based on, for example, amino acid sequence of the target, such as amino acid sequences of the N- or C-terminus. Polypeptides of the invention contain at least one loop-variant PDZ binding domain. In some embodiments, polypeptides can contain additional functional regions such as a "reporter group" and/or an "effector domain."

As used herein, "engineered" refers to a polypeptide of the invention containing at least one PDZ domain that has been modified by in vitro manipulation. For example, an "engineered" polypeptide or PDZ domain is non-naturally occurring, such as a PDZ domain whose properties, including sequence, have been changed by in vitro mutation according to any suitable method including rational design or directed evolution. The engineered polypeptide typically has properties that differ from a naturally occurring polypeptide, such as different binding specificity or affinity. An "engineered" PDZ domain includes an "evolved" PDZ domain that has been subject to directed evolution or other in vitro evolution techniques.

As used herein, "PDZ domain" refers to a protein module capable of binding to a target protein by recognition of the target's C-terminal or N-terminal amino acid sequence. PDZ domains are typically 85-95 amino acids in length and are found naturally in a variety of organisms ranging from bacteria to humans. An example PDZ domain is the PDZ domain of hCASK having the sequence SEQ ID NO: 2. A further example PDZ domain is the third PDZ domain of human Dlg1, such as shown within SEQ ID NO:4 (see FIG. 1). Other PDZ domains, according to the invention, have homology to the PDZ domains of SEQ ID NO: 1, SEQ ID NO: 2, SEQ ID NO: 3, SEQ ID NO: 4, or SEQ ID NO: 5, such as at least about 50% identity using BLAST (default parameters). The name PDZ is derived from: PSD-95 (Cho et al., Neuron 9:929-942, 1992), Dlg-A (Woods and Bryant, Cell 66:451-464, 1991) and ZO-1 (Itoh et al., J. Cell. Biol. 121:491-502, 1993), each of which contains three such domains. PDZ domains have also been called GLGF repeats or DHRs and are identified in a variety of proteins (Ponting and Phillips, Trends Biochem. Sci. 20:102-103, 1995). The first PDZ domain of the Na+/H+ exchanger regulatory protein (NHERF) has been shown to interact with the carboxyl terminus of CFTR, the cystic fibrosis transmembrane conductance regulator (Moyer et al., 2000, J Biol Chem, 275: 27069-74.). A PDZ domain of PTPL1 has been shown to interact with the C-terminal tail of the membrane receptor Fas (Sato et al., 1995) and PDZ domains of PSD-95 bind to the C-termini of the NMDAreceptor and Shaker-type K⁺ channels (Kim et al., Nature 378:85-88, 1995; Komau et al., Science 269:1737-1740, 1995). The crystal structures of different PDZ domains have been published (e.g., Doyle et al., Cell 0.85:1067-1076, 1996; Morais Cabral et al., Nature 382:649-652, 1996; (Karthikeyan et al., 2001, J Biol Chem, 276: 19683-6)). The PDZ domain of human CASK/LIN-2, also called hCASK, is well studied: its substrate specificity has been investigated (Cohen et al., 1998, J Cell Biol, 142: 129-38.) and its crystal structure determined (Daniels et al., 1998, Nat Struct Biol, 5: 317-25.). One skilled in the art can readily recognize and identify a PDZ domain, for example, by using the CD-Search computer program available at www.ncbi.nlm.gov/Structure/cdd/cdd.shtml, the NIH's free "Conserved Domain Database and Search Service".

A "PDZ loop-variant" is defined herein as an engineered PDZ domain in which one or more amino acids have been substituted or inserted in one or more of the PDZ domain's loops. In the literature, loops are sometimes referred to as "reverse turns" (Creighton, 1993). Loops of particular interest to PDZ domains include loops β12, α2β6, β23, and β5α2. These loops range in length from one to about 18 amino acids, 15, 12, 11, 10, 9, 8, 7, 6, 5, 4, 3, or 2 amino acids, depending on which particular PDZ domain and which particular loop one examines, and are located between certain α-helices and β-strands. According to the naming convention herein, loop β12 is located between β-strand 1 and β-strand 2; loop α2β6 is found between helix α2 and strand β-6; and so on. PDZ loop-variants can be created using directed evolution or other protein engineering methods, and can be evolved, for instance, to bind to novel molecular targets such as disease-causing toxins or microbial antigens. Loop regions can be assigned by one skilled in the art to certain segments of the amino acid sequence of a PDZ domain by calculating the phi and psi angles of the amino acids in its three-dimensional structure; elements of regular conformation such as α-helices and β-strands can be readily identified by the phi and psi angles of their amino acids (see for example (Creighton, 1993), p. 183, FIG. 5.7 and table 5.2), and loops can be assigned to amino acid segments existing between these regular secondary structure elements. Alternatively, loop regions can be identified by alignment of PDZ domain amino acid sequences if the secondary structures of at least one such sequence have been mapped onto its amino acid sequence. Collections, or "libraries", of loop-variants can be prepared using "in vitro evolution" methods, as described below.

The term "substitution" is defined here as the replacement of one or more amino acids in a polypeptide resulting from two or more nucleotide changes in the corresponding polynucleotide. This is typically achieved by the mutation of two or more nucleotides in one or more codons in a polynucleotide sequence coding for a polypeptide of interest. Such mutations can affect as few as two nucleotides, and as many as about 54 nucleotides in a polynucleotide, corresponding to as few as one but as many as about 18 codons, 15 codons, 12, 11, 10, 9, 8, 7, 6, 5, 4, 3, or 2 codons. Codons can be substituted with codons of unique sequence to create unique novel polypeptide variants, or with degenerate codons encoding many possible sequences to create collections, or "libraries", of polypeptide variants. Substitutions can be made anywhere in a polypeptide, including, for example substitutions in loops of polypeptides, such as loops of PDZ domains. Within a loop, substitutions can be made to any one or more amino acid residues.

The term "insertion" is defined here as the introduction of one or more amino acids between two amino acids in a polypeptide. This is typically achieved by the insertion of one or more codons in a polynucleotide sequence coding for a polypeptide of interest. Insertions of as few as one codon to as many as 18 codons, 15 codons, 12, 11, 10, 9, 8, 7, 6, 5, 4, 3, or 2 codons are possible. Codons of unique sequence can be inserted to create unique novel polypeptide variants, or degenerate codons encoding many possible sequences can be inserted to create collections, or "libraries", of polypeptide variants. Insertions can be made between any two amino acids in a polypeptide, including, for example, insertions in loops of polypeptides, such as loops of PDZ domains. Within a loop, insertions can be made between any two amino acid residues.

As used herein, a "bivalent" PDZ loop-variant is defined as a PDZ loop-variant capable of simultaneously binding to two target molecules. These bivalent PDZ loop-variants can bind simultaneously to two copies of the same target, or two different targets. For instance, a bivalent PDZ loop-variant can bind to a cancer-related target as well as a target chemotherapeutic having tumoricidal properties. As a further example, a bivalent PDZ loop-variant can bind to a pathogen target as well as a target having antibiotic or antiviral properties. As a further example, a bivalent PDZ loop-variant can bind to a serum protein and a target chemotherapeutic having antibiotic or anticancer activities. A bivalent PDZ loop-variant can bind one target through its canonical ligand-binding pocket and another target through one of its modified loops.

PDZ domains can also be changed by an in vitro evolution process to generate an evolved PDZ domain having a particular desired function that is different from the original function. The "evolved" PDZ domain can be evolved from any parent PDZ domain, such as a naturally-occurring PDZ domain, to change binding affinity or specificity of the parent PDZ domain for a preselected target. In some embodiments, the evolved PDZ domain is evolved from the hCASK PDZ domain. In some embodiments, the evolved PDZ domain is evolved from the third PDZ domain of human Dlg1, the structure of which is discussed in Cabral et al., Nature 382: 649-652, 1996. In some embodiments, the evolved PDZ domain is evolved from the first PDZ domain of NHERF, the Na+/H+ Exchanger Regulatory Factor, the atomic structure of which is discussed in (Karthikeyan et al., 2001, J Biol Chem, 276: 19683-6).

Sequences of any polypeptides herein are provided in standard format and are read left to right in the amino to carboxy direction.

A "reporter group," as used herein, is defined as a molecular moiety that is readily detected, directly or indirectly, and is attached covalently to a polypeptide, such as a polypeptide of the invention containing a PDZ domain. Examples of reporter groups include polynucleotides that are readily detected, for example, by polymerase chain reaction (PCR); biotin which is readily detected with streptavidin conjugated to horseradish peroxidase; fluorescent proteins such as the Green Fluorescent Protein (GFP), which is detected by fluorescence spectroscopy; epitope tags such as the influenza hemagglutinin peptide HA epitope corresponding to the amino acid sequence YPYDVPDYA (SEQ ID NO: 7), detected with antibodies binding specifically to this epitope; dual function epitope/enzyme tags such as GST (glutathione S-transferase), which can be detected indirectly using an antibody specific to this protein, or directly using a colorimetric assay measuring enzymatic GST activity; enzymes such as alkaline phosphatase, which can be detected using chemiluminescence. Reporter groups also include radioactive isotopes and imaging agents, such as chelated heavy metals, which can be used for in vivo diagnostics and imaging. Numerous other examples of molecular entities which can be used as reporter groups are known in the art.

An "effector domain", as used herein, is defined as a protein domain, or other molecular moiety, which adds a function other than detection to a polypeptide to which it is covalently attached. An effector domain can be the Fc domain of immunoglobulins, which mediates function of the immune system such as opsonization, phagocytosis and activation of complement. Other effector domains include toxins such as cholera toxin, which can be used to kill cells recognized by the polypeptide to which the effector domain is attached. Other toxins can include, for example, botulin toxin, diphtheria toxin, anthrax toxin, ricin, *Clostridium difficile* toxin, and the like. Other examples of effector domains include protein transduction domains which enable proteins to which they are attached to cross the cell membrane and to locate in the cytoplasm of mammalian cells, as described, for example, in Wadia and Dowdy, 2002, Curr Op Biotechnol, 13:52-6 and references therein, in which short sequences such as the Tat protein's transduction domain (YGRKKRRQRRR (SEQ ID NO: 8) single letter amino acid code) and other arginine-rich basic peptides are described. Another example effector domain is serum albumin. Yet other examples of effector domains include RNA molecules which can be used to mediate selective inactivation of gene expression via RNA interference (RNAi); chemotherapeutic agents such as bleomycin, which can be used to kill cancer cells; radioactive isotopes which can also be used to kill cancer cells; and the like. More than one effector domain can be linked to a single PDZ domain in a polypeptide of the invention. Effector domains such as PDZ domains binding to serum proteins or other host proteins can modulate pharmacokinetics of the protein to which it is fused. Thus, a PDZ domain having therapeutic activity can be fused to another PDZ domain acting as an effector domain modulating pharmacokinetics. Other molecules, such as polyethylene glycol (PEG), can also be used as effector domains to modulate pharmacokinetics or reduce immunogenicity (Nucci et al., *Advan. Drug Del. Rev.* 6, 133, 1991, and Inada et al., *J Bioactive Compat. Polymer* 5, 343, 1990). PEG can be attached to other proteins as described in U.S. Pat. No. 6,677,438.

As used herein, the term "variant" is meant to indicate a polypeptide differing from another polypeptide by one or more amino acid substitutions or insertions resulting from engineered mutations in the gene coding for the polypeptide. One skilled in the art can readily recognize and identify a variant of a PDZ domain, for example, by using the CD-Search computer program available at www.ncbi.nlm.gov/Structure/cdd/cdd.shtml, the NIH's free "Conserved Domain Database and Search Service" which can identify protein domains such as the PDZ domain and its variants. A polypeptide is typically no longer considered a variant of a parent polypeptide when the degree of homology between these polypeptides falls below about 40%, as ascertained for example by using the program BLAST to align two sequences (default parameters) described by Tatiana A. Tatusova and Thomas L. Madden (1999), "Blast 2 sequences—a new tool for comparing protein and nucleotide sequences", FEMS Microbiol Lett. 174:247-250. In some embodiments, variants have at least about 50%, at least about 60%, at least about 70%, at least about 80%, at least about 85%, at least about 90%, at least about 95%, at least about 97%, at least about 98%, at least about 99% homology with the parent polypeptide, as ascertained for example by using the program BLAST to align two sequences (default parameters). In some embodiments, a parent polypeptide can be evolved in vitro using directed evolution to yield one or more variants of the parent polypeptide. These variants can have new or improved properties compared to the parent polypeptide or be useful in generating further variants.

The term "peptide" refers to a compound of 2 to about 50 subunit amino acids, amino acid analogs, or peptidomimetics. The subunits can be linked by peptide bonds. In other embodiments, the subunit can be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. In some embodiments, peptides can have from 2 to about 30, 2 to about 20, 2 to about 10, 9, 8, 7, 6, 5, 4, 3 or 2 subunit amino acids, amino acid analogs, or peptidomimetics.

As used herein, the term "in vitro evolution", or "directed evolution" refers to a method of generating two or more different polypeptides (e.g., a "library" of polypeptides) by accelerating mutation rates and/or recombination events of polynucleotides encoding parent polypeptides under in vitro conditions and screening or selecting the resulting new polypeptides. The process of directed evolution has been described in detail (Joo et al., Chem. Biol., 1999, 6, 699-706; Joo et al., Nature, 1999, 399, 670-673; Miyazaki et al., J. Mol. Evol., 1999, 49, 716-720; Chen et al., Proc. Natl. Acad. Sci. USA, 1993, 90, 5618-5622; Chen et al., Biotechnology, 1991, 9, 1073-1077; You et al., Protein Eng, 1996, 9, 77-83; each of which is incorporated herein by reference in its entirety). In general, the method involves the steps of 1) creating a population of mutant polynucleotides; 2) screening this population for individual nucleotides which have a desired property such as coding for a protein with improved binding affinity; and repeating these two steps, if necessary, until a desired improvement is achieved. Many methods to introduce mutations exist and are described in the literature (Leung et al., Technique, 1989, 1, 11-15; Delagrave et al., Protein Eng., 1993, 6, 327-331; each of which is incorporated herein by reference in its entirety). Other methods known in the art, such as overlap PCR as discussed by (Horton et al., 1990, Biotechniques, 8: 528-35.) and (Xu et al., 2002, Chem Biol, 9: 933), can be used to insert degenerate or random codons in polynucleotides, or to substitute certain codons with degenerate or random codons. Alternatively the desired insertions or substitutions can be achieved by synthesis of an entire gene or gene fragment, including specified nucleotide positions which are randomized or degenerate, as offered by companies such as Blue Heron (www.blueheronbio.com) and DNA2.0 (www.dnatwopointo.com). Similarly, there are many ways to screen or select mutants for a desired property (Smith, *Science*, 1985, 228, 1315; Hanes & Pluckthun, *Proc. Natl. Acad. Sci. USA*, 1997, 94, 4937; Xu et al., *Chem. Biol*, 2002, 9, 933; Joo et al., Chem. Biol., 1999, 6, 699-706; Joo et al., Nature, 1999, 399, 670-673; Miyazaki et al., J. Mol. Evol., 1999, 49, 716-720; Chen et al., Proc. Natl. Acad. Sci. USA, 1993, 90, 5618-5622; Chen et al., Biotechnology, 1991, 9, 1073-1077; You et al., Protein Eng, 1996, 9, 77-83; Marrs et al., Curr. Opin. Microbiol., 1999, 2, 241-245; and U.S. Pat. No. 5,914, 245).

As used herein, the term "parent polypeptide" describes a polypeptide which is a starting component of an in vitro evolution process. "Parent polypeptide" distinguishes the starting polypeptides from evolved forms of the polypeptides ("evolved polypeptides"). For example, a "parent PDZ domain" refers to a PDZ domain that is used as a starting point for generating different (or evolved) PDZ domains by in vitro evolution. Likewise, an "evolved PDZ domain" describes a PDZ domain that is the product of an in vitro evolution process. A parent PDZ domain can be a naturally-occurring domain.

As used herein, the term "parent polynucleotide" describes a polynucleotide which is a starting component of an in vitro evolution process. "Parent polynucleotide" distinguishes the starting polynucleotides from evolved forms of the polynucleotides ("evolved polynucleotides"). For example, a "parent PDZ polynucleotide" refers to a polynucleotide encoding a PDZ domain that is used as a starting point for generating different (e.g., evolved) PDZ domains (variant PDZ domains) by in vitro evolution. Likewise, an "evolved PDZ polynucleotide" describes a polynucleotide encoding a PDZ domain which is the product of an in vitro evolution process.

As used herein, "library" refers to a collection of two or more different polypeptides or polynucleotides. The collection of polypeptides or polynucleotides of a library can be prepared by any of numerous methods including de novo synthesis, error-prone PCR, recursive ensemble mutagenesis, combinatorial mutagenesis, and other mutagenesis methods such as gene shuffling and the like.

As used herein, "disease state" or "disease" or "disorder," used interchangeably, refers to any of numerous pathological conditions of the mind or body. The disease state can be infectious or non-infectious. The disease state can be symptomatic or non-symptomatic infection by a pathogen. The disease state can be chronic or acute, and also includes abnormal immune responses (e.g., allergies). Example disease states include pathogen infection or toxicity due to exposure to pathogen-related toxins such as bacterial (e.g., botulism, anthrax), fungal, or viral infection. Further, example disease states include non-infectious diseases such as cancers (prostate, breast, etc.), cardio-pulmonary diseases (myocardial infarction, atherosclerosis, etc.), neurodegenerative diseases (Alzheimer's, Parkinson's, ALS, etc.), allergic responses (e.g., asthma, hives, etc.) and the like.

As used herein, a "target" or "target molecule" refers to any molecular entity to which a further molecular entity binds. In some embodiments, the target is a polypeptide or peptide. In some embodiments, the target is a small molecule or a solid support. In further embodiments, at least one terminus, such as the C-terminus, is at least partially exposed. The target can be associated with a biological state such as a disease (pathogenic or non-pathogenic) or disorder in a plant or animal (e.g., a mammal) as well as the presence of a pathogen. When a target is "associated with" a certain biological state, the presence or absence of target or the presence of a certain amount of target (e.g., outside of normal levels), can identify the biological state. For example, a target can be a protein, such as prostate-specific antigen (PSA), that is differentially expressed in certain cancer cells. In some embodiments, the target can be amyloid beta (involved in Alzheimer's disease) or beta 2-microglobulin (involved in dialysis-associated amyloidosis) or peptides corresponding to the C-terminal 3 to 12 residues of these polypeptides. As a further example, a target can include proteins such as IgE (immunoglobulin E), IL-5, or IL-17, associated with diseases such as asthma. As a further example, a target can include proteins such as IgA, IgD, IgM, IgG. In further embodiments, the target can be interleukin, cytokine, amyloid beta, beta 2-microglobulin, VEGF, streptavidin of *Streptomyces avidinii*, F protein of RSV, VP1 of Coxsackievirus A9, Vpr of HIV, PSA, or growth hormone.

As a further example, a target can include a protein such as anaphylatoxins C3a and C5a which are described in: Humbles, et al. *Nature* 406, 998-1001 (2000); Kawamoto, et al., *J Clin Invest*, 114, 399-407 (2004); Gerard, et al. Complement in allergy and asthma. *Curr Opin Immunol* 14, 705-708 (2002); Ames, et al., *J Biol Chem* 271, 20231-20234 (1996); Fitch, et al., *Circulation* 100, 2499-2506 (1999); Shernan, et al., *Ann Thorac Surg* 77, 942-949 (2004).

As a further example, a target can include proteins, such as endothelial growth factors like VEGF, associated with diseases such as macular degeneration and cancers. As a further example, a target can include growth hormones such as human growth hormone, associated with acromegaly. In another example, targets such as creatine kinase, troponin I and troponin T are associated with myocardial infarction. In a further example, a target can be a protein of a pathogen such as a virus, bacterium, fungus, or single-celled organism. Thus, in some embodiments, the target can be the F1 and F2 subunits of respiratory syncytial virus fusion protein, or VP1 of Coxsackievirus A9 (CAV9), or Vpr of HIV. In some embodiments, the target can be a protein found in the exosporium of *Bacillus anthracis*, such as protein BclA. In other embodiments, the target can be one or more proteins making up a toxin such as botulinum neurotoxins of various serotypes (including heavy and light chains, as described for example in Singh, Nat. Struct. Biol., 2000, 7:617-9, and references therein), tetanus neurotoxin, or anthrax toxin (including lethal factor, protective antigen and edema factor, as reviewed for example in Stubbs, Trends Pharmcol Sci, 2002, 23:539-41, and references therein). In yet further embodiments, the target can be a polypeptide having a C-terminal sequence of EFYA. Additional examples of targets include other polypeptides used to treat or diagnose disease. Example polypeptides used to treat or diagnose disease include, for example, Enfuvirtide (commercially known as Fuzeon), interferons, monoclonal antibodies such as Rituximab (Rituxan), and the like. In some further embodiments, targets may include serum proteins such as human serum albumin and transferrin.

The term "intermediate target" refers to a target that is different from the ultimately desired target but is sufficiently similar so as to aid in preparing the desired polypeptide of the invention. For example, the intermediate target can be a large polypeptide of at least about 50 amino acids. As a further example, the intermediate target can be a peptide fragment of the desired target. For example, the peptide fragment can contain 3, 4, 5, or 6 amino acids. Peptides can often be easier to manipulate than large proteins. In other embodiments, the intermediate target can be a target in which its amino acid sequence has about 20 to about 80 percent homology with the amino acid sequence of the ultimately desired target. In this way, in vitro evolution of the polypeptide containing a PDZ domain can be coaxed in a desired direction. Several different intermediate targets can be used in the in vitro evolution process. For example, intermediate targets having increasing percent identity can be used in successive rounds of evolution.

As used herein, the term "pathogen" refers to any microorganism, virus or prion causing disease in humans, other animals or plants, including commercially important domesticated animals and crops. Pathogens include, for example, bacteria such as *Bacillus anthracis, Escherichia coli* O:157, *Yersinia pestis, Helicobacter pylori, Clostridium difficile, Streptococcus pneumoniae, Staphylococcus aureus, Mycobacterium tuberculosis, Mycobacterium bovis, Clostridium botulinum, Clostridium tetani* and the like. Viral pathogens include, for example, human immunodeficiency viruses (HIV), hepatitis A, B and C viruses, (HAV, HBV, HCV), respiratory syncytial virus (RSV), poliovirus, Coxsackievirus A9 (CAV9), smallpox virus, CMV (cytomegalovirus), flaviviruses, papillomaviruses, coronaviruses (e.g., SARS-CoV), influenza virus, viral plant pathogens such as alfalfa mosaic virus, tobacco mosaic virus, and the like. Other microbial pathogens include parasites and fungi such as, for example, *Plasmodium falciparum* (malaria) and the fungus *Candida albicans*, respectively, and the like. Prion pathogens include transmissible spongiform encephalopathies such as bovine spongiform encephalopathy (BSE), Creutzfeld-Jacob disease (CJD) and the like.

As used herein, an "enzyme" is defined as any of numerous proteins that catalyze specific chemical reactions. Examples of enzymes include β-lactamases, polymerases, proteases, endonucleases, glutathione S-transferase (GST), alkaline phosphatase, and the like. Many toxins, such as cholera toxin, botulin toxin and the like, are or comprise enzymes.

As used herein, a "fluorescent protein" is defined as a protein having ability to fluoresce in the visible wavelengths of the electromagnetic spectrum (i.e., from about 300 nm to about 700 nm). Examples of fluorescent proteins include the Green Fluorescent Protein (GFP) and its derivatives, as well as DsRed and other proteins and their derivatives available commercially from BD Biosciences under the trademark "Living Colors".

As used herein, an "epitope" is defined as a molecular region of an antigen capable of eliciting an immune response and of combining with the specific antibody produced by such a response. Epitopes can be peptides, polynucleotides, polypeptides, polysaccharides and the like.

As used herein, the term "antibody" includes polyclonal antibodies and monoclonal antibodies as well as fragments thereof. Antibodies include, but are not limited to mouse, rat, and rabbit, human, chimeric antibodies and the like. The term "antibody" also includes antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski, et al. *Proc. Natl. Acad. Sci.,* 1985, 82, 8653 or Spira, et al., *J. Immunol. Methods,* 1984, 74, 307.

The invention also provides fragments of the polyclonal and monoclonal antibodies described above. These "antibody fragments" typically retain some ability to selectively bind with its antigen or immunogen. Such antibody fragments can include, but are not limited to: Fab, Fab', F(ab')$_2$, Fv, and SCA. An example of a biologically active antibody fragment is a CDR region of the antibody. Methods of making these fragments are known in the art, see for example, Harlow and Lane (1988), infra.

The antibodies of this invention also can be modified to create chimeric antibodies and humanized antibodies (Oi, et al., *BioTechniques,* 1986, 4(3), 214 which is incorporated herein by reference in its entirety). Chimeric antibodies are, for example, those in which the various domains of the antibodies' heavy and light chains are coded for by DNA from more than one species.

The isolation of other hybridomas secreting monoclonal antibodies with the specificity of the monoclonal antibodies of the invention can also be accomplished by one of ordinary skill in the art by producing anti-idiotypic antibodies (Herlyn, et al., *Science,* 1986, 232:100, which is incorporated herein by reference in its entirety). An anti-idiotypic antibody is an antibody which recognizes unique determinants present on the monoclonal antibody produced by the hybridoma of interest.

Antibodies according to the present invention can also include genetically engineered antibody fragments. For example, molecular clones of variable domains of antibodies can be transformed into single-chain variable domains (scFv), diabodies, Fab (Barbas et al., *Proc. Natl. Acad. Sci. USA,* 1992, 9, 10164), bivalent Fab (Fab'), etc., using standard recombinant DNA technology. Phage display (Smith, *Science,* 1985, 228, 1315), ribosome display (Hanes & Pluckthun, *Proc. Natl. Acad. Sci. USA,* 1997, 94, 4937) and mRNA display (Xu et al., *Chem. Biol,* 2002, 9, 933) can be used in vitro to select antibodies with desired affinity and/or specificity.

Laboratory methods for producing polyclonal antibodies and monoclonal antibodies, as well as deducing their corresponding nucleic acid sequences, are known in the art, see, e.g., *ANTIBODIES, A LABORATORY MANUAL* (Harlow and Lane eds. (1988)) and Sambrook et al. *MOLECULAR CLONING: A LABORATORY MANUAL,* 2$^{nd}$ edition (1989), each of which is incorporated herein by reference in its entirety. The monoclonal antibodies of the present invention can be biologically produced by introducing an antigen such as a protein or a fragment thereof into an animal, e.g., a mouse or a rabbit. The antibody producing cells in the animal are isolated and fused with myeloma cells or heteromyeloma cells to produce hybrid cells or hybridomas.

As used herein, "nucleic acids" or "polynucleotides" refer to polymeric forms of nucleotides or analogs thereof, of any length. The polynucleotides can contain deoxyribonucleotides, ribonucleotides, and/or their analogs. Nucleotides can have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, dsRNA, and the like. Polynucleotide sequences presented herein are provided in standard format.

Nucleic acid molecules further include oligonucleotides, such as antisense molecules, probes, primers and the like. Oligonucleotides typically have from about 2 to about 100, 8 to about 30, or 10 to about 28 nucleotides or analogs thereof.

Nucleic acid molecules can also contain modified backbones, modified bases, and modified sugars, such as for enhancing certain desirable properties such as in vivo stability, binding affinity, etc. Modifications of nucleic acids are well known in the art and include, for example, modifications described in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361, 5,625,050, 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437, 5,677,439, 5,539,082; 5,714,331, 5,719,262, 5,489,677, 5,602,240, 5,034,506, 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633, 5,700,920, 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617, 5,681,941, 5,750,692, 5,013,830; 5,149,797; 5,220,007; 5,256,775; 5,366,878; 5,403,711; 5,491,133; 5,565,350; 5,623,065; 5,652,355; 5,652,356; and 5,700,922, each of which is incorporated herein by reference in its entirety.

Isolation, preparation, and manipulation of nucleic acids, is well known in the art and is well described in Sambrook, et al., supra.

The present invention also relates to "vectors" which include the isolated DNA molecules of the present invention, "host cells" which are genetically engineered with the recombinant vectors, or which are otherwise engineered to produce the polypeptides of the invention, and the production of evolved PDZ domains, or derivatives thereof, by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In one embodiment, the DNA of the invention is operatively associated with an appropriate heterologous regulatory element (e.g., promoter or enhancer), such as, the phage lambda PL promoter, the E. coli lac, trp, and tac promoters, the SV40 early and late promoters and promoters of retroviral LTRs, to name a few. Other suitable promoters will be known to the skilled artisan.

In embodiments in which vectors contain expression constructs, these constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Vectors preferred for use in bacteria include pQE70, pQE60 and pQE9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Selection of appropriate vectors and promoters for expression in a host cell is a well known procedure and the requisite techniques for expression vector construction, introduction of the vector into the host and expression in the host are routine skills in the art.

The present invention also relates to host cells containing the vector constructs discussed herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins.

Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Sambrook et al., supra.

As used herein, the phrase "optimization" is intended to mean any process whereby a DNA sequence encoding a translation product (polypeptide or protein) is changed to improve the expression level of this protein without altering its amino acid sequence. For instance, gene optimization can be achieved by computational methods (e.g., Fuglsang, Protein Expr Purif. 2003, 31:247-9). An alternative method of gene optimization amounts to a specialized application of directed evolution described by Stemmer et al., Gene, 1993, 123:1-7. Example expression systems include bacteria (e.g., E. coli) and yeast.

As used herein, the term "cell-free selection" or "cell-free screening assay" is defined as any affinity selection method which does not involve the direct use of living cells. Examples of cell-free selections include ribosome display (Hanes & Pluckthun, Proc. Natl. Acad. Sci. USA, 1997, 94, 4937) and mRNA display (Xu et al., Chem. Biol, 2002, 9, 933). Phage display, which requires the transformation of DNA into cells in order to create selectable libraries, does not constitute an example of cell-free selection.

As used herein, the term "contacting" refers to the bringing together of designated substances (e.g., a sample and a polypeptide of the invention) such that the substances can interact at the molecular level sufficient to show, for example, binding affinity.

Methods of Preparing Polypeptides

The present invention further provides methods of preparing a polypeptide using in vitro evolution techniques. For example, a polypeptide containing a loop-variant PDZ domain can be prepared by creating a library of polypeptides from one or more parent polypeptides also containing a PDZ domain. One or more polypeptides having new or improved binding affinity for a desired target can then be identified from the library. In some embodiments, the identified polypeptides can be used to create a further library from which another polypeptide can be identified, potentially having different or even greater binding affinity for the selected target. This process of mutagenesis and selection can be repeated iteratively several times.

Binding affinities (reported as dissociation constant, or $K_d$) of evolved PDZ domains in polypeptides of the invention can be from about 1 mM to about 1 fM, about 1000 nM to about 1 fM, about 100 nM to about 1 fM, 50 nM to about 1 fM, about 20 nM to about 1 fM, about 15 nM to about 1 fM, about 10 nM to about 1 fM, about 5 nM to about 1 fM or about 1 nM to about 1 fM. In some embodiments, the binding affinity of a loop-variant PDZ domain according to the present invention for a preselected target is less than about 100 nM, less than about 50 nM, less than about 20 nM, less than about 15 nM or less than about 10 nM. Affinity can be measured by surface plasmon resonance (SPR) as implemented, for example, on a Biacore instrument (Biacore). Identification of library members that bind to the desired target can be carried out by any suitable methods. In some embodiments, polypeptides can be identified by phage display, or in a cell-free selection such as mRNA display.

In further embodiments, the present invention provides a method of preparing a polypeptide containing a PDZ domain by forming a library of polypeptides from one or more parent polypeptides comprising a PDZ domain; selecting a first selected polypeptide from the library, where the first selected polypeptide has binding affinity to an intermediate target. The intermediate target can have, for example, 20% to 80% (e.g., 20%, 30%, 40%, 50%, 60%, 70% or 80%) sequence identity with the desired target. A further library of polypeptides can then be created from the first selected polypeptide and the process can be repeated until a library yields a polypeptide capable of binding with the desired target. The intermediate target can act as an evolutionary guide for the evolving polypeptide, and can be particularly useful when sequence of the target is substantially different from sequence of the optimal binder to the parent polypeptide. One or more intermediate targets can be used, and different intermediate targets can be used for each iteration.

Therapeutic and Prophylactic Methods

Methods of treatment according to the present invention can include both prophylaxis and therapy. Prophylaxis or therapy can be accomplished by administration to a patient of therapeutic agents such as polypeptides containing loop-variant PDZ domains prepared, for example, by the directed evolution methods described herein. In some embodiments, methods of treatment include administration of a polypeptide of the invention. In other embodiments, methods of treatment include administration of a peptide which can be bound by a polypeptide of the invention. The therapeutic agent can be administered at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human.

A disease or disorder, such as a viral infection, cancer, allergy, or other pathological condition associated with a target, can be diagnosed using criteria generally accepted in the art, including, for example, the presence of a malignant tumor or elevated white blood cell count. Therapeutic agents can be administered either prior to or following surgical removal of primary tumors and/or treatment such as administration of radiotherapy or conventional chemotherapeutic drugs. In further embodiments, therapeutic agents such as polypeptide of the invention can also be administered prior to infection by an infectious agent such as a virus, bacteria, or other pathogen.

Within certain embodiments, therapy can be immunotherapy, which can be active immunotherapy in which treatment relies on the in vivo stimulation of the endogenous host immune system (e.g., stimulation of endogenous effector cells) to react against tumors or infected cells with the administration of binding proteins prepared according to the methods described herein. Within other embodiments, immunotherapy can be passive immunotherapy, in which treatment involves the delivery of agents with, for example, immune reactivity (such as evolved PDZ domains fused to an Fc domain or conjugated to an antibody or antibody fragment) that can directly or indirectly mediate antitumor, anti-inflammatory, or other effects and do not necessarily depend on an intact host immune system. Examples of effector cells include T cells, T lymphocytes (such as CD8+ cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages).

The therapeutic agents prepared according to the methods described herein can be combined with a pharmaceutically acceptable carrier to produce a pharmaceutical composition. As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, *Remington's Pharmaceutical Sciences*, Chapter 43, 14th Ed., Mack Publishing Co, Easton Pa. 18042, USA).

Therapeutic and Prophylactic Compositions and Uses

Much like antibodies and antibody fragments, polypeptides containing loop-variant PDZ domains and their derivatives can be useful in the treatment of numerous disorders including, for example, cancer, inflammatory disorders, such as adult respiratory distress syndrome (ARDS), hypovolemic shock, ulcerative colitis, rheumatoid arthritis, and others, as shown in Table 1 which provides a list of diseases and molecular targets addressed by therapeutic antibodies.

TABLE 1

Monoclonal antibody-based therapeutics
(Nature Biotechnology, 2003, 21, 868).

| Product | Initial indication | Year approved |
|---|---|---|
| Bexxar (tositumomab; radiolabelled monoclonal antibody directed against CD20, produced in a mammalian cell line.) | Treatment of CD20 positive follicular non-Hodgkin lymphoma | 2003 (US) |
| Xolair (Omalizumab; rIgG1k Mab that binds IgE, produced in CHO cells) | Asthma | 2003 (US) |
| Humira (adalimumab; r human Mab (antiTNF) created using phage display technology and produced in a mammalian cell line) | Rheumatoid arthritis | 2002 (US) |
| Zevalin (Ibritumomab Tiuxetan; murine Mab produced in a CHO cell line, targeted against the CD20 antigen. A radiotherapy agent.) | Non-Hodgkin lymphoma | 2002 (US) |

TABLE 1-continued

Monoclonal antibody-based therapeutics
(Nature Biotechnology, 2003, 21, 868).

| Product | Initial indication | Year approved |
|---|---|---|
| Mabcampath (EU) or Campath (US) (alemtuzumab; a humanized monoclonal antibody directed against CD52 surface antigen of B-lymphocytes.) | Chronic lymphocytic leukemia | 2001 (EU, US) |
| Mylotarg (gemtuzumab zogamicin; a humanized antibody-toxic antibiotic conjuage targeted against CD33 antigen found on leukemic blast cells.) | Acute myeloid leukemia | 2000 (US) |
| Herceptin (trastuzumab, humanized antibody directed against human epidermal growth factor receptor 2 (HER2)) | Treatment of metastatic breast cancer if tumor overexpresses HER2 protein | 1998 (US), 2000 (EU) |
| Remicade (infliximab, chimeric mAb directed against TNF-alpha | Treatment of Crohn disease | 1998 (US), 1999 (EU) |
| Synagis (palivizumab, humanized mAb directed against an epitope on the surface of respiratory syncytial virus.) | Prophylaxis of lower respiratory disease caused by syncytial virus in pediatric patients | 1998 (US), 1999 (EU) |
| Zenapax (daclizumab, humanized mAb directed against the alpha-chain of the IL-2 receptor) | Prevention of acute kidney transplant rejection | 1997 (US), 1999 (EU) |
| Humaspect (Votumumab, human mAb directed against cytokeratin tumor-associated antigen) | Detection of carcinoma of the colon or rectum | 1998 (EU) |
| Mabthera (Rituximab, chimeric mAb directed against CD20 surface antigen of B lymphocytes. See also Rituxan.) | Non-Hodgkin lymphoma | 1998 (EU) |
| Simulect (basiliximab, chimeric mAb directed against the alpha-chain of the IL-2 receptor) | Prophylaxis of acute organ rejection in allogeneic renal transplantation | 1998 (EU) |
| LeukoScan (Sulesomab, murine mAb fragment (Fab) directed against NCA 90, a surface granulocyte nonspecific cross-reacting antigen.) | Diagnostic imaging for infection/inflammation in bone of patients with osteomyelitis | 1997 (EU) |
| Rituxan (rituximab chimeric mAb directed against CD20 antigen found on the surface of B lymphocytes) | Non-Hodgkin lymphoma | 1997 (US) |
| Verluma (Nofetumomab murine mAb fragments (Fab) directed against carcinoma-associated antigen.) | Detection of small-cell lung cancer | 1996 (US) |
| Tecnemab KI (murine mAb fragments (Fab/Fab2 mix) directed against HMW-MAA) | Diagnosis of cutaneous melanoma lesions | 1996 (EU) |
| ProstaScint (capromab-pentetate, murine mAb directed against the tumor surface antigen PSMA) | Detection/staging/follow-up of prostate adenocarcinoma | 1996 (US) |
| MyoScint (imiciromab-pentetate, murine mAb fragment directed against human cardiac myosin) | Myocardial infarction imaging agent | 1996 (US) |
| CEA-scan (arcitumomab, murine mAb fragment (Fab), directed against human carcinoembryonic antigen, CEA) | Detection of recurrent/metastatic colorectal cancer | 1996 (US, EU) |
| Indimacis 125 (Igovomab, murine mAb fragment (Fab2) directed against the tumor-associated antigen CA 125) | Diagnosis of ovarian adenocarcinoma | 1996 (EU) |
| ReoPro (abciximab, Fab fragments derived from a chimeric mAb, directed against the platelet surface receptor GPIIb/IIIa) | Prevention of blood clots | 1994 (US) |
| OncoScint CR/OV (satumomab pendetide, murine mAb directed against TAG-72, a tumor-associated glycoprotein) | Detection/staging/follow-up of colorectal and ovarian cancers | 1992 (US) |
| Orthoclone OKT3 (Muromomab CD3, murine mAb directed against the T-lymphocyte surface antigen CD3) | Reversal of acute kidney transplant rejection | 1986 (US) |

Therapeutic formulations of polypeptides of the invention or derivatives thereof can be prepared for storage by mixing the polypeptide or derivative thereof having the desired degree of purity with optional pharmaceutically acceptable carriers, excipients, or stabilizers (see, e.g., *Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

Polypeptides of the invention or derivatives thereof for in vivo administration are preferably sterile. This can be readily accomplished by filtration through sterile filtration membranes, prior to or following lyophilization and reconstitution. The polypeptides of the invention or derivatives thereof ordinarily will be stored in lyophilized form or in solution.

Therapeutic polypeptide compositions generally are placed into a container having a sterile access port, for example, an intravenous solution bag or vial having a stopper pierceable by a hypodermic injection needle.

The route of polypeptide administration can be carried out in accord with known methods, e.g., inhalation, injection or infusion by intravenous, intraperitoneal, intracerebral, intramuscular, intraocular, intraarterial, or intralesional routes, by enema or suppository, or by sustained release systems as noted below. The polypeptide or its derivative is given systemically or at a site of inflammation.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919 and EP 58,481), copolymers of L-glutamic acid and gamma ethyl-L-glutamate (Sidman et al., *Biopolymers,* 1983, 22, 547), poly (2-hydroxyethyl-methacrylate) (Langer et al., *J. Biomed. Mater. Res.,* 1981, 15, 167 and Langer, *Chem. Tech.,* 1982, 12, 98), ethylene vinyl acetate (Langer et al., supra) or poly-D-(−)-3-hydroxybutyric acid (EP 133,988). Sustained-release compositions also include liposomally entrapped evolved PDZ domain or derivative thereof. Liposomes containing an evolved PDZ domain or derivative thereof can be prepared by methods known per se: DE 3,218,121; Epstein et al., *Proc. Natl. Acad. Sci. U.S.A.,* 1985, 82, 3688; Hwang et al., *Proc. Natl. Acad. Sci. U.S.A.,* 1980, 77, 4030; EP 52,322; EP 36,676; EP 88,046; EP 143,949; EP 142,641; U.S. Pat. Nos. 4,485,045 and 4,544,545; and EP 102,324. Ordinarily the liposomes are of the small (about 200-800 Angstroms) unilamelar type in which the lipid content is greater than about 30 mole percent cholesterol, the selected proportion being adjusted for the most efficacious therapy.

An "effective amount" of a polypeptide of the invention to be employed therapeutically will depend, for example, upon the therapeutic objectives, the route of administration, and the condition of the patient. Accordingly, it may be necessary for the therapist to titer the dosage and modify the route of administration as required to obtain the optimal therapeutic effect. Typically, the clinician will administer the polypeptide until a dosage is reached that achieves the desired effect. The progress of this therapy is easily monitored by conventional assays.

In the treatment and prevention of a disease or disorder, the polypeptide composition can be formulated, dosed, and administered in a fashion consistent with good medical practice. Factors for consideration in this context include the particular disorder being treated, the particular mammal being treated, the clinical condition of the individual patient, the cause of the disorder, the site of delivery of the polypeptide, the particular type of polypeptide, the method of administration, the scheduling of administration, and other factors known to medical practitioners. The "therapeutically effective amount" of polypeptide to be administered can be governed by such considerations, and is the minimum amount necessary to prevent, ameliorate, or treat the inflammatory disorder. Such amount is preferably below the amount that is toxic to the host or renders the host significantly more susceptible to infections.

As a general proposition, the initial pharmaceutically effective amount of the polypeptide administered parenterally per dose can be in the range of about 0.1 to 50 mg/kg of patient body weight per day, with the typical initial range of polypeptide used being 0.3 to 20 mg/kg/day, more preferably 0.3 to 15 mg/kg/day. As noted above, however, these suggested amounts of polypeptide are subject to therapeutic discretion.

The polypeptide of the invention need not be, but is optionally formulated with one or more agents currently used to prevent or treat the disease or disorder in question. For example, in rheumatoid arthritis, a polypeptide can be given in conjunction with a glucocorticosteroid, or for cancer, a polypeptide can be given in conjunction with a chemotherapeutic. The polypeptide can also be formulated with one or more other polypeptides of the invention to provide a therapeutic "cocktail."

Methods of Detection

The invention further provides a method for detecting a disease, disease-causing pathogen or disorder such as cancer in a sample, comprising contacting the sample with a polypeptide containing a loop-variant PDZ domain that binds to a target in the sample, where the target is associated with the disease, pathogen, or disorder. The target can be, for example, a nucleic acid or protein encoded thereby. The target can be a substance, such as a peptide or protein that is produced directly or indirectly by a pathogen, including their toxins and the like. The sample can be an environmental sample, or a tissue from a mammal, such as human, bovine, equine, canine, feline, porcine, and ovine tissue. In some embodiments, the tissue is human. The tissue can comprise a tumor specimen, cerebrospinal fluid, or other suitable specimen such a tissue likely to contain the target of interest. In one embodiment, the method comprises use of an ELISA type assay that employs an evolved loop-variant PDZ domain or derivative thereof by the methods described herein to detect the presence of target in a specimen. This method can also be used to monitor target levels in a tissue sample of a patient. For example, the suitability of a therapeutic regimen for initial or continued treatment can be determined by monitoring target levels according to this method.

The invention further provides a method for detecting a disease, including a disease-causing pathogen or a disease such as cancer, in a patient by administering a polypeptide of the invention to the patient and detecting binding of the polypeptide in the patient. In some embodiments, the administered polypeptide further contains a reporter group, such as a radioactive moiety, chelated heavy metal, or other imaging agent to facilitate detection of binding of the polypeptide in the patient. Binding of polypeptide in the patient can be observed as localization of the polypeptide in certain tissues containing the desired target. For example, a polypeptide of the invention that is capable of specifically binding to a cancer marker such as a polypeptide differentially expressed from certain cancer cells can reveal the presence of a tumor or diseased tissue by detection of localization of the polypeptide. Methods for scanning a patient, such as a human patient, are well known in the art and include radiography, MRI, and related techniques.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. These methods are described in the following publications. See, e.g., Sambrook, et al., *Molecular Cloning. A Laboratory Manual,* 2nd edition (1989); *Current Protocols in Molecular Biology* (F. M. Ausubel et al. eds. (1987)); the series *Methods in Enzymology* (Academic Press, Inc.); *PCR: A Practical Approach* (M. MacPherson et al. IRL Press at Oxford University Press (1991)); *PCR 2. A Practical Approach* (M. J. MacPherson et al., eds. (1995)); *Antibodies,*

*A Laboratory Manual* (Harlow and Lane eds. (1988)); *Animal Cell Culture* (R. I. Freshney ed. (1987)); and *Phage Display: A Laboratory Manual* (C. F. Barbas III et al., (2001)), each of which is incorporated herein by reference in its entirety.

Methods of Purification

The present invention further provides a method of purifying a protein comprising contacting said protein with an immobilized polypeptide containing a loop-variant PDZ domain, wherein the immobilized polypeptide has binding affinity for the protein. Suitable binding affinities (reported as dissociation constant, or $K_d$) include from about 1 mM to about 1 fM, about 1000 nM to about 1 fM, about 100 nM to about 1 fM, 50 nM to about 1 fM, about 20 nM to about 1 fM, about 15 nM to about 1 fM, about 10 nM to about 1 fM, about 5 nM to about 1 fM or about 1 nM to about 1 fM. In some embodiments, the binding affinity is less than about 100 nM, less than about 50 nM, less than about 20 nM, less than about 15 nM or less than about 10 nM.

The following examples are presented to illustrate the present invention and to assist one of ordinary skill in making and using the same. The examples are not intended in any way to otherwise limit the scope of the invention.

EXAMPLES

Example 1

Insertion of Six Amino Acids in Loop β23 of a PDZ Domain

Figure 3:
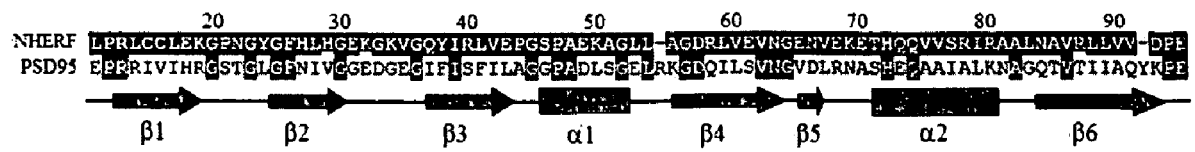
FIG. 3. Assignment of secondary structure to amino acid sequence of NHERF PDZ1 (SEQ ID NO: 5, (Ferrer et al., 2005, Protein Eng Des Sel, 18: 165-173)) and PSD95 PDZ3 (SEQ ID NO: 6, (Ferrer et al., 2005, Protein Eng Des Sel, 18: 165-173)). As defined herein, loops flanked by secondary structure elements are named by concatenating the names of the flanking elements, e.g., the loop between strands β1 and β2 is called loop β12, the loop between strand β5 and helix α2 is called loop β5α2.

To verify that the β23 loop of PDZ1 domain of NHERF mutant H9 (Ferrer et al., 2005, Protein Eng Des Sel, 18: 165-173) could still bind its ligand despite an insertion, 6 amino acids were inserted in this loop between residues G33 and K34 (using numbering scheme of FIG. 3).

This insertion was done by overlap PCR. Four oligonucleotides were synthesized: I-S (TGCCACCCGCAGTTCTG-CAAGGTGGGCCAGTACATC (SEQ ID NO: 9)), G3 (GGAGCTGCATGTGTCAGAGG (SEQ ID NO: 10)), G5 (CACGTTTGGTGGTGGCGACC (SEQ ID NO: 11)), and I-AS (GCAGAACTGCGGGTGGCAGCCCTTCTC-CCCATGCAG (SEQ ID NO: 12)). These oligos were used to amplify two DNA fragments by PCR using as a template the gene encoding a mutant of the first PDZ domain of NHERF cloned in a modified version of the pGEX-2TK expression vector. The resulting fragments were fused by overlap PCR to yield a loop-variant version of the NHERF PDZ1 gene encoding the six amino acid sequence CHPQFC (SEQ ID NO: 13) inserted between residues G33 and K34. The overlap PCR product was digested with enzymes BamHI and EcoRI and ligated into the similarly digested pGEX-2TK modified plasmid. The ligated DNA was transformed into *E. coli* XL1-Blue and one of the resulting transformants, designated H2, was picked for characterization by DNA sequencing, revealing the desired sequence with no additional unwanted mutations.

The GST-PDZ fusion protein expressed by clone H2 was partially characterized. The DNA of clone H2 was transformed into *E. coli* strain BL21 [DE3] and the resulting transformant induced in 1 mL culture volume using 0.1 mM IPTG for 2.5 hours at 30° C. with shaking at 300 rpm. The cells were harvested from the culture medium and lysed using BugBuster (Novagen). Batch affinity purification was carried out using 50 μl of glutathione affinity resin (Novagen), eluting the bound protein in reduced glutathione elution buffer. SDS-PAGE analysis of the eluted protein shows comparable expression level to similarly purified PDZ protein that has no loop insertion. The eluted protein was tested by ELISA for binding to N-terminally biotinylated peptide HRRSARYLDTVL (SEQ ID NO: 14) bound to 0.1 μg of streptavidin coated onto each well of an ELISA plate. Serial dilutions of the protein were added to wells in which the peptide was present or absent (negative controls) and immuno-detection of a C-terminal hexahistidine tag provided by the modified pGEX-2TK vector was carried out using a horseradish peroxidase-conjugated antibody (Roche). As expected, control samples of clone H2 which were not induced with IPTG showed no binding to the peptide. Surprisingly, protein from the induced sample of the PDZ loop-variant H2 was capable of binding strongly and specifically to peptide HRRSARYLDTVL (SEQ ID NO: 14) despite the 6 amino acid insertion in loop β23. These data indicated that the insertion of 6 amino acids in loop β23 is well tolerated by NHERF PDZ1 and does not interfere with binding of the protein to a peptide ligand.

Example 2

Creation of PDZ Loop-Variant Library

Phage Display of the First PDZ Domain of NHERF Mutant H9.

The first PDZ domain of rabbit protein NHERF mutant H9 was prepared for phage display by cloning the corresponding DNA into vector pCANTAB5E (GE Healthcare). The sequence of NHERF PDZ1 cloned in vector pCANTAB5E was confirmed by DNA sequencing. The ability of the phage-displayed PDZ domain to bind specifically its ligand (N-terminal biotinylated peptide having the sequence "HRRSARYLDTVL" (SEQ ID NO: 14)) was shown by phage ELISA.

Mutagenesis of Loop β23

A random hexapeptide sequence is inserted in loop β23 of NHERF PDZ1 mutant H9. A PCR product is synthesized using NHERF PDZ1 mutant H9, cloned in pCANTAB5E, as a template and oligonucleotide B23X6S (CTGCATGGG-GAGAAGGGCNNKNNKNNKNNKNNKNN-KAAGGTGGGCCAGTACATC (SEQ ID NO: 15)), as a 5' primer, and oligonucleotide pCAN3' (CGATCTAAAGTTTTGTCGTC (SEQ ID NO: 16)) as 3' primer, where the symbol 'K' represents a 1:1 mixture of bases G and T, and the symbol 'N' represents a 1:1:1:1 mixture of all four bases A, C, G, and T. The resulting PCR product is purified by gel electrophoresis and gel extraction, then assembled into a full-length mutated PDZ domain loop-variant pool by overlap PCR with another PCR product obtained using oligos pCAN5' (CATGATTACGC-CAAGCTTTGG (SEQ ID NO: 17)) and B23X6AS (GCCCT-TCTCCCCATGCAG (SEQ ID NO: 18)), and purified separately. The resulting overlap PCR product is digested with restriction enzymes SfiI and NotI and ligated into vector pCANTAB5E also digested with the same enzymes. DNA is ligated using the Fastlink rapid ligation kit (Epicentre, Madison, Wis.). The ligated DNA is then transformed into *E. coli* strain DH5αFT (Invitrogen) by electroporation. Several electroporations are carried out to create a large library (large number of independent transformants). Transformants are recovered in SOB for 1 hour at 37° C. with shaking at 225 rpm, then the growth medium is adjusted to SOBAGT (i.e., growth medium SOB containing 2% glucose, 100 μg/mL ampicillin, and 10 μg/mL tetracycline) and the transformed cells are allowed to grow at 30° C. for about 16 to 20 hours with shaking at 250 rpm.

Example 3

Affinity Selection of PDZ Loop-Variant Binding Streptavidin of *Streptomyces avidinii*

Display Phage Rescue

Phage displaying PDZ loop-variants are rescued from the cell suspension resulting from the transformation described in Example 2. To prepare phage, 1 mL of the cell suspension is added to 9 mL of 2×YTGAT (i.e., 2×YT containing 2% glucose, 100 µg/mL ampicillin, and 10 µg/mL tetracycline), also containing 4×10$^{10}$ pfu of M13K07 helper phage. The resulting culture is incubated 1 hour at 37° C. with shaking. Cells are then removed by centrifugation at 1000 g for 15 minutes, resuspended in 10 mL of 2×YT containing 100 µg/mL ampicillin, 50 µg/mL kanamycin, and 10 µg/mL tetracycline, and shaken at 30° C. overnight. The next day, phage are precipitated from the culture supernatant using PEG/NaCl and resuspended in PBS.

Affinity Selection

Affinity selection of PDZ loop-variants is carried out by applying an aliquot of the phage suspension to two wells of a polystyrene multiwell plate (Nunc) coated with ~1 µg of streptavidin (Jackson Immunoresearch Laboratories, West Grove, Pa.). Phage displaying the PDZ loop-variant library are panned according to standard methods (e.g., Barbas et al., 2001) through 5 rounds of panning. Phage binding specifically to the streptavidin-coated wells are allowed to infect *E. coli* DH5αFT simply by adding log-phase cells to the well and incubating them for 15 minutes. The input phage titer (number of phage added to a well) and output phage titer (phage removed from well) from each round are determined. The ratio of output phage to input phage for each round of panning typically shows a clear trend of phage amplification after Round 3 or 4, suggesting selection of mutants specific for the target.

Loop-Variant Screening

A phage ELISA is performed on about 20 randomly chosen clones from each of panning rounds 3, 4 and 5 to verify that the selection is successfully amplifying loop-variants binding specifically to streptavidin. Log-phase DH5αFT cultures are infected with the mutant phage output from each panning round. An aliquot of this infected culture is then plated onto agar-containing medium and allowed to grow 16 hours. Multiple clones (colonies) are picked, grown in 96-well polypropylene culture plates, infected with helper phage, and the resulting culture supernatant used in a phage ELISA. Several clones from round 5 produce a strong binding signal to streptavidin and are chosen for further characterization.

Loop-Variant Characterization

Phage are purified by PEG/NaCl precipitation from three mutants as well as wildtype controls and tested against streptavidin and bovine serum albumin (BSA) by phage ELISA. Each mutant shows dramatically improved ELISA signal for streptavidin compared to NHERF PDZ1H9, and only weak binding to BSA. These PDZ loop-variants are therefore capable of specifically binding to streptavidin.

Confirmation of Streptavidin Binding

Characterized mutants showing binding to streptavidin are then further characterized; their ability to bind streptavidin as purified protein is confirmed. Phagemid DNA of the selected PDZ loop-variants is purified per standard methods, digested with EcoRI and BamHI and the resulting variant PDZ gene fragment is ligated to pGEX-2TK DNA digested with the same restriction enzymes. The resulting ligated DNA is transformed into *E. coli* strain BL21[DE3] to yield clones containing plasmid pGEX-PDZ-variant. These clones are grown to an OD600 of about 0.55 and induced using 0.1 mM IPTG for 4 hours at 30° C. The induced cells are pelleted by centrifugation, frozen at −80° C., thawed, and lysed using BugBuster reagent (Novagen, EMD Biosciences, San Diego, Calif.). PDZ loop-variant-GST fusion protein is purified from the lysate via affinity chromatography using glutathione sepharose affinity medium. Purified loop-PDZ variant-GST fusion protein is then tested for its ability to bind streptavidin by using the PDZ loop-variant-GST fusion as an affinity reagent, wherein streptavidin is coated onto the wells of a multi-well plate in an ELISA format, and binding of the loop-variant to the well is detected using anti-GST antibody (GE Healthcare) labeled with horseradish peroxidase, and a peroxidase substrate such as ABTS (Sigma), according to standard methods.

Further confirmation of specific binding of purified PDZ loop-variant to streptavidin is made by a surface plasmon resonance-based detection method as implemented on a BIAcore instrument (BIAcore, Uppsala, Sweden).

Example 4

Construction of PDZ Loop-Variant Fusion Proteins and their Use as Affinity Reagents Any of the evolved PDZ variants isolated in example 3 can be made into translational fusions essentially as described for PDZ loop-variant-GST fusions of the example. Any of the resulting fusion proteins can be used as affinity reagents for detection of the peptides or proteins which these PDZ variants have been evolved to bind, for instance in an ELISA-like assay, as described in the example.

Example 5

Sequences

```
SEQ ID NO: 19.
Sequence of NHERF mutant H9.
LPRLCCLEKGPNGYGFHLHGEKGKVGQYIGLVVPGSPAEKAGLLAGDRLV

EVNGENVEKETHQQVVSRIRAALNAVCLLVVDPE

SEQ ID NO: 20.
Sequence of NHERF PDZ loop-variant H2, wherein the
6 amino acid insertion is underlined.
LPRLCCLEKGPNGYGFHLHGEKGCHPQFCKVGQYIGLVVPGSPAEKAGLL

AGDRLVEVNGENVEKETHQQVVSRIRAALNAVCLLVVDPE

SEQ ID NO: 21.
Sequence of NHERF PDZ loop-variant library, where
X represents any of the twenty amino acids.
LPRLCCLEKGPNGYGFHLHGEKGXXXXXXKVGQYIGLVVPGSPAEKAGLL

AGDRLVEVNGENVEKETHQQVVSRIRAALNAVCLLVVDPE

SEQ ID NO: 22.
Nucleotide sequence encoding amino acid sequence
of SEQ ID NO 21, flanked by SfiI and NotI
restriction sites for convenient in-frame cloning
into pCANTAB5E vector.
GCGGCCCAGCCGGCCGGATCCCTGCCCCGGCTCTGCTGCCTGGAGAAGGG

GCCGAACGGCTACGGCTTCCACCTGCATGGGAGAAGGGCNNKNNKNNKN

NKNNKNNKAAGGTGGGCCAGTACATCGGGCTGGTGGTGCCCGGCTCTCCG

GCCGAGAAGGCGGGGCTGCTGGCCGGGGACCGGCTGGTGGAGGTGAACGG

CGAGAACGTGGAGAAGGAGACCCACCAGCAGGTGGTGAGCCGCATCCGCG
```

-continued

CCGCGCTCAACGCCGTGTGCCTGCTGGTGGTCGACCCCGAGACGGACGAG

CAGCTGGAATTCGCGGCCGCAGGTGCG

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety

---

What is claimed is:

1. A polypeptide comprising SEQ ID NO: 21.

2. A polynucleotide comprising SEQ ID NO: 22.

* * * * *

SEQUENCE LISTING

```
<160> NUMBER OF SEQ ID NOS: 23

<210> SEQ ID NO 1
<211> LENGTH: 85
<212> TYPE: PRT
<213> ORGANISM: Homo sapiens

<400> SEQUENCE: 1

Ile Phe Glu Val Glu Leu Ala Lys Asn Asp Asn Ser Leu Gly Ile Ser
1               5                   10                  15

Val Thr Gly Gly Val Asn Thr Ser Val Arg His Gly Gly Ile Tyr Val
                20                  25                  30

Lys Ala Val Ile Pro Gln Gly Ala Ala Glu Ser Asp Gly Arg Ile His
            35                  40                  45

Lys Gly Asp Arg Val Leu Ala Val Asn Gly Val Ser Leu Glu Gly Ala
        50                  55                  60

Thr His Lys Gln Ala Val Glu Thr Leu Arg Asn Thr Gly Gln Val Val
65                  70                  75                  80

His Leu Leu Leu Glu
                85

<210> SEQ ID NO 2
<211> LENGTH: 81
<212> TYPE: PRT
<213> ORGANISM: Homo sapiens

<400> SEQUENCE: 2

Ser Arg Leu Val Gln Phe Gln Lys Asn Thr Asp Glu Pro Met Gly Ile
1               5                   10                  15

Thr Leu Lys Met Asn Glu Leu Asn His Cys Ile Val Ala Arg Ile Met
                20                  25                  30

His Gly Gly Met Ile His Arg Gln Gly Thr Leu His Val Gly Asp Glu
            35                  40                  45

Ile Arg Glu Ile Asn Gly Ile Ser Val Ala Asn Gln Thr Val Glu Gln
        50                  55                  60

Leu Gln Lys Met Leu Arg Glu Met Arg Gly Ser Ile Thr Phe Lys Ile
65                  70                  75                  80

Val

<210> SEQ ID NO 3
<211> LENGTH: 80
<212> TYPE: PRT
<213> ORGANISM: Homo sapiens
<220> FEATURE:
<223> OTHER INFORMATION: domain of NHERF

<400> SEQUENCE: 3

Pro Arg Leu Cys Cys Leu Glu Lys Gly Pro Asn Gly Tyr Gly Phe His
1               5                   10                  15

Leu His Gly Glu Lys Gly Lys Leu Gly Gln Tyr Ile Arg Leu Val Glu
                20                  25                  30
```

```
Pro Gly Ser Pro Ala Glu Lys Ala Gly Leu Leu Ala Gly Asp Arg Leu
            35                  40                  45

Val Glu Val Asn Gly Glu Asn Val Glu Lys Glu Thr His Gln Gln Val
 50                  55                  60

Val Ser Arg Ile Arg Ala Ala Leu Asn Ala Val Arg Leu Leu Val Val
 65                  70                  75                  80

<210> SEQ ID NO 4
<211> LENGTH: 81
<212> TYPE: PRT
<213> ORGANISM: Homo sapiens

<400> SEQUENCE: 4

Pro Arg Lys Val Val Leu His Arg Gly Ser Thr Gly Leu Gly Phe Asn
 1               5                  10                  15

Ile Val Gly Gly Glu Asp Gly Glu Gly Ile Phe Ile Ser Phe Ile Leu
                20                  25                  30

Ala Gly Gly Pro Ala Asp Leu Ser Gly Glu Leu Arg Lys Gly Asp Arg
            35                  40                  45

Ile Ile Ser Val Asn Ser Val Asp Leu Arg Ala Ala Ser His Glu Gln
 50                  55                  60

Ala Ala Ala Ala Leu Lys Asn Ala Gly Gln Ala Val Thr Ile Val Ala
 65                  70                  75                  80

Gln

<210> SEQ ID NO 5
<211> LENGTH: 84
<212> TYPE: PRT
<213> ORGANISM: Oryctolagus cuniculus

<400> SEQUENCE: 5

Leu Pro Arg Leu Cys Cys Leu Glu Lys Gly Pro Asn Gly Tyr Gly Phe
 1               5                  10                  15

His Leu His Gly Glu Lys Gly Lys Val Gly Gln Tyr Ile Arg Leu Val
                20                  25                  30

Glu Pro Gly Ser Pro Ala Glu Lys Ala Gly Leu Leu Ala Gly Asp Arg
            35                  40                  45

Leu Val Glu Val Asn Gly Glu Asn Val Glu Lys Glu Thr His Gln Gln
 50                  55                  60

Val Val Ser Arg Ile Arg Ala Ala Leu Asn Ala Val Arg Leu Leu Val
 65                  70                  75                  80

Val Asp Pro Glu

<210> SEQ ID NO 6
<211> LENGTH: 86
<212> TYPE: PRT
<213> ORGANISM: Homo sapiens

<400> SEQUENCE: 6

Glu Pro Arg Arg Ile Val Ile His Arg Gly Ser Thr Gly Leu Gly Phe
 1               5                  10                  15

Asn Ile Val Gly Gly Glu Asp Gly Glu Gly Ile Phe Ile Ser Phe Ile
                20                  25                  30

Leu Ala Gly Gly Pro Ala Asp Leu Ser Gly Glu Leu Arg Lys Gly Asp
            35                  40                  45

Gln Ile Leu Ser Val Asn Gly Val Asp Leu Arg Asn Ala Ser His Glu
 50                  55                  60

Gln Ala Ala Ile Ala Leu Lys Asn Ala Gly Gln Thr Val Thr Ile Ile
```

```
                65                  70                  75                  80
Ala Gln Tyr Lys Pro Glu
                    85
```

<210> SEQ ID NO 7
<211> LENGTH: 9
<212> TYPE: PRT
<213> ORGANISM: Artificial Sequence
<220> FEATURE:
<223> OTHER INFORMATION: Influenza hemagglutinin peptide

<400> SEQUENCE: 7

```
Tyr Pro Tyr Asp Val Pro Asp Tyr Ala
 1               5
```

<210> SEQ ID NO 8
<211> LENGTH: 11
<212> TYPE: PRT
<213> ORGANISM: Artificial Sequence
<220> FEATURE:
<223> OTHER INFORMATION: Naturally occuring peptideTat protein's
      transduction domain

<400> SEQUENCE: 8

```
Tyr Gly Arg Lys Lys Arg Arg Gln Arg Arg Arg
 1               5                  10
```

<210> SEQ ID NO 9
<211> LENGTH: 36
<212> TYPE: DNA
<213> ORGANISM: Artificial Sequence
<220> FEATURE:
<223> OTHER INFORMATION: Synthetically generated oligonucleotide

<400> SEQUENCE: 9
tgccacccgc agttctgcaa ggtgggccag tacatc                             36

<210> SEQ ID NO 10
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 10
ggagctgcat gtgtcagagg                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 11
cacgtttggt ggtggcgacc                                               20

<210> SEQ ID NO 12
<211> LENGTH: 36
<212> TYPE: DNA
<213> ORGANISM: Artificial Sequence
<220> FEATURE:
<223> OTHER INFORMATION: Synthetically generated oligonucleotide

<400> SEQUENCE: 12
gcagaactgc gggtggcagc ccttctcccc atgcag                             36

```
<210> SEQ ID NO 13
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 13

Cys His Pro Gln Phe Cys
  1               5

<210> SEQ ID NO 14
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 14

His Arg Arg Ser Ala Arg Tyr Leu Asp Thr Val Leu
  1               5                  10

<210> SEQ ID NO 15
<211> LENGTH: 54
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 19, 20, 22, 23, 25, 26, 28, 29, 31, 32, 34, 35
<223> OTHER INFORMATION: n = a, t, g or c

<400> SEQUENCE: 15
ctgcatgggg agaagggcnn knnknnknnk nnknnkaagg tgggccagta catc         54

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
cgatctaaag ttttgtcgtc                                               20

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
catgattacg ccaagctttg g                                             21

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
gcccttctcc ccatgcag                                                 18

<210> SEQ ID NO 19
```

```
<211> LENGTH: 84
<212> TYPE: PRT
<213> ORGANISM: Homo sapiens

<400> SEQUENCE: 19

Leu Pro Arg Leu Cys Cys Leu Glu Lys Gly Pro Asn Gly Tyr Gly Phe
1               5                   10                  15

His Leu His Gly Glu Lys Gly Lys Val Gly Gln Tyr Ile Gly Leu Val
            20                  25                  30

Val Pro Gly Ser Pro Ala Glu Lys Ala Gly Leu Leu Ala Gly Asp Arg
        35                  40                  45

Leu Val Glu Val Asn Gly Glu Asn Val Glu Lys Glu Thr His Gln Gln
50                  55                  60

Val Val Ser Arg Ile Arg Ala Ala Leu Asn Ala Val Cys Leu Leu Val
65                  70                  75                  80

Val Asp Pro Glu

<210> SEQ ID NO 20
<211> LENGTH: 90
<212> TYPE: PRT
<213> ORGANISM: Artificial Sequence
<220> FEATURE:
<223> OTHER INFORMATION: Synthetically generated peptide

<400> SEQUENCE: 20

Leu Pro Arg Leu Cys Cys Leu Glu Lys Gly Pro Asn Gly Tyr Gly Phe
1               5                   10                  15

His Leu His Gly Glu Lys Gly Cys His Pro Gln Phe Cys Lys Val Gly
            20                  25                  30

Gln Tyr Ile Gly Leu Val Val Pro Gly Ser Pro Ala Glu Lys Ala Gly
        35                  40                  45

Leu Leu Ala Gly Asp Arg Leu Val Glu Val Asn Gly Glu Asn Val Glu
    50                  55                  60

Lys Glu Thr His Gln Gln Val Val Ser Arg Ile Arg Ala Ala Leu Asn
65                  70                  75                  80

Ala Val Cys Leu Leu Val Val Asp Pro Glu
                85                  90

<210> SEQ ID NO 21
<211> LENGTH: 90
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 24, 25, 26, 27, 28, 29
<223> OTHER INFORMATION: Xaa = any amino acid

<400> SEQUENCE: 21

Leu Pro Arg Leu Cys Cys Leu Glu Lys Gly Pro Asn Gly Tyr Gly Phe
1               5                   10                  15

His Leu His Gly Glu Lys Gly Xaa Xaa Xaa Xaa Xaa Xaa Lys Val Gly
            20                  25                  30

Gln Tyr Ile Gly Leu Val Val Pro Gly Ser Pro Ala Glu Lys Ala Gly
        35                  40                  45

Leu Leu Ala Gly Asp Arg Leu Val Glu Val Asn Gly Glu Asn Val Glu
    50                  55                  60

Lys Glu Thr His Gln Gln Val Val Ser Arg Ile Arg Ala Ala Leu Asn
65                  70                  75                  80
```

```
Ala Val Cys Leu Leu Val Val Asp Pro Glu
                85                  90

<210> SEQ ID NO 22
<211> LENGTH: 327
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 91, 92, 94, 95, 97, 98, 100, 101, 103, 104, 106, 107
<223> OTHER INFORMATION: N = a, t, c or g

<400> SEQUENCE: 22
gcggcccagc cggccggatc cctgccccgg ctctgctgcc tggagaaggg gccgaacggc      60
tacggcttcc acctgcatgg ggagaagggc nnknnknnkn nknnknnkaa ggtgggccag     120
tacatcgggc tggtggtgcc cggctctccg gccgagaagg cggggctgct ggccggggac     180
cggctggtgg aggtgaacgg cgagaacgtg gagaaggaga cccaccagca ggtggtgagc     240
cgcatccgcg ccgcgctcaa cgccgtgtgc ctgctggtgg tcgaccccga gacggacgag     300
cagctggaat tcgcggccgc aggtgcg                                         327

<210> SEQ ID NO 23
<211> LENGTH: 82
<212> TYPE: PRT
<213> ORGANISM: Artificial Sequence
<220> FEATURE:
<223> OTHER INFORMATION: Consensus sequence

<400> SEQUENCE: 23

Val Arg Thr Val Thr Leu Arg Lys Asp Pro Gly Gly Gly Leu Gly Phe
  1               5                  10                  15

Ser Leu Arg Gly Gly Lys Asp Ser Gly Gly Ile Phe Val Ser Arg
             20                  25                  30

Val Glu Pro Gly Gly Pro Ala Glu Arg Gly Gly Leu Arg Val Gly Asp
             35                  40                  45

Arg Ile Leu Glu Val Asn Gly Val Ser Val Glu Gly Leu Thr His Glu
 50                  55                  60

Glu Ala Val Glu Leu Leu Lys Asn Ser Gly Asp Glu Val Thr Leu Thr
 65                  70                  75                  80

Val Arg
```